(12) United States Patent
Tamura et al.

(10) Patent No.: US 10,551,398 B2
(45) Date of Patent: Feb. 4, 2020

(54) SPECIMEN CONTAINER INCLINATION CORRECTION MECHANISM, AND METHOD FOR CONTROLLING SAME

(71) Applicant: Hitachi High-Technologies Corporation, Tokyo (JP)

(72) Inventors: Kazuma Tamura, Tokyo (JP); Toshiki Yamagata, Tokyo (JP); Hiroki Ihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 179 days.

(21) Appl. No.: 15/566,799

(22) PCT Filed: Mar. 16, 2016

(86) PCT No.: PCT/JP2016/058227
§ 371 (c)(1),
(2) Date: Oct. 16, 2017

(87) PCT Pub. No.: WO2016/174949
PCT Pub. Date: Nov. 3, 2016

(65) Prior Publication Data
US 2018/0120339 A1 May 3, 2018

(30) Foreign Application Priority Data
Apr. 27, 2015 (JP) .................................. 2015-089934

(51) Int. Cl.
*G01N 35/04* (2006.01)
*G01N 35/00* (2006.01)

(52) U.S. Cl.
CPC ......... *G01N 35/04* (2013.01); *G01N 35/0099* (2013.01); *G01N 2035/041* (2013.01);
(Continued)

(58) Field of Classification Search
CPC ..... G01N 2035/0494; G01N 2035/041; G01N 35/04–2035/0498; B25J 15/0028; B25J 15/0052–0066; B01L 9/50
See application file for complete search history.

(56) References Cited

U.S. PATENT DOCUMENTS

| 6,255,614 | B1 * | 7/2001 | Yamakawa | ............ G01N 35/04 |
| | | | | 209/509 |
| 2003/0061911 | A1 * | 4/2003 | Niwayama | ................ B67B 7/02 |
| | | | | 81/3.2 |

(Continued)

FOREIGN PATENT DOCUMENTS

| CN | 101218493 A | 7/2008 |
| JP | 2001-96483 A | 4/2001 |

(Continued)

OTHER PUBLICATIONS

Machine Translation JP2004061136 (Year: 2019).*
(Continued)

*Primary Examiner* — Justin Seo
*Assistant Examiner* — David L Singer
(74) *Attorney, Agent, or Firm* — Mattingly & Malur, PC (57) ABSTRACT

When a specimen transport system transfers a specimen container to a transport rack, the specimen container located at a position adjacent to a transfer position thereof is inclined on the rack, and there is a possibility that the one specimen container may collide with the other specimen container when the one specimen container is transferred. Where the transferred specimen container is inclined after being transferred, and a specimen container transfer mechanism is raised from the location, there is also a possibility that the one specimen container and the other specimen container adjacent thereto may collide with each other. Consequently, an inclination angle of a transferred specimen container and a specimen container adjacent thereto is corrected by load- (Continued)

ing a specimen container inclination correction mechanism including two inclination correction units at a specimen container transfer position. In this manner, a contact risk is suppressed and a stable transfer process is made possible.

7 Claims, 7 Drawing Sheets

(52) U.S. Cl.
CPC ........... *G01N 2035/0412* (2013.01); *G01N 2035/0494* (2013.01)

(56) References Cited

U.S. PATENT DOCUMENTS

| | | | |
|---|---|---|---|
| 2005/0123445 A1* | 6/2005 | Blecka | G01N 35/0099 422/64 |
| 2009/0142844 A1 | 6/2009 | Le Comte | |
| 2013/0136569 A1* | 5/2013 | Rosmarin | G01N 35/0099 414/618 |
| 2013/0239527 A1 | 9/2013 | Clarke et al. | |
| 2014/0008927 A1* | 1/2014 | Rousseau | B29C 49/4205 294/90 |

FOREIGN PATENT DOCUMENTS

| | | |
|---|---|---|
| JP | 2004-61136 A | 2/2004 |
| JP | 2004-061140 A | 2/2004 |

OTHER PUBLICATIONS

Extended European Search Report received in corresponding European Application No. 16786226.7 dated Nov. 14, 2018.
International Search Report of PCT/JP2016/058227 dated Jul. 12, 2016.
Chinese Office Action received in corresponding Chinese Application No. 201680024165.X dated Jun. 26, 2019.

\* cited by examiner

SPECIMEN CONTAINER INCLINATION CORRECTION MECHANISM, AND METHOD FOR CONTROLLING SAME

TECHNICAL FIELD

The present invention relates to a mechanism provided with a function to correct inclination of a specimen container in transferring the specimen container of a specimen transport system and an automatic analysis device.

BACKGROUND ART

In clinical tests, a specimen transport system transports a specimen container to an automatic analysis device through a specimen transport line after specimen pretreatment (specimen allocation and centrifugation) and dispensing treatment (child specimen generation) are performed on the specimen contained in the specimen container. The transported specimen container is subjected to an analysis process in the automatic analysis device. Thereafter, the specimen container passes through the specimen transport line again, and is transported for post-treatment (specimen capping and storage).

At this time, the specimen transport system and the automatic analysis device which are manufactured by mutually different companies are often connected to each other. In this case, the specimen container is transferred to a specimen transport rack used inside the automatic analysis device manufactured by the other company, and is allocated to the analysis device. The transferred specimen container is inclined inside the rack unless a posture of the specimen container is corrected by the rack. Consequently, treatment such as dispensing, transfer, and analysis cannot be stably performed.

In order to solve the above-described problem, PTL 1 discloses the following. In transferring the specimen container, the specimen container installed in a row adjacent to a position of a transfer destination is separated from the transfer destination position by a regulation member so as not to disturb the transfer.

CITATION LIST

Patent Literature

PTL 1: JP-A-2004-61140

SUMMARY OF INVENTION

Technical Problem

The regulation member disclosed in PTL 1 can regulate the posture of the specimen container installed in the row adjacent to the position of the transfer destination (transfer destination position), but cannot correct the inclination of the transferred specimen container itself. Therefore, when the specimen container is inclined after the specimen container is completely transferred and a transfer mechanism completely transferring the specimen container is separated from a transfer position, there is a possibility that the transfer mechanism may come into contact with the inclined specimen container. In addition, in a case where the transfer container is held adjacent to a position before the specimen container is transferred (former position prior to transfer), if the specimen container is inclined, there is a possibility that the transfer mechanism may come into contact with the specimen container held adjacent to the former position prior to transfer. If the specimen container and the transfer mechanism come into contact with each other in this way, there is a risk that a specimen analysis result may be delayed due to device operation break and the specimen may be damaged.

In view of the above-described problems, the invention aims to provide a specimen transfer device which eliminates a risk that a transfer target specimen container and a specimen container held around the transfer target specimen container and a transfer mechanism may come into contact with each other, when the specimen container is transferred to a transfer destination position or when the specimen container is removed from a former position prior to transfer.

Solution to Problem

In order to solve the above-described problems, the invention includes the following characteristics.

That is, there is provided a specimen transport system including a correction mechanism that corrects inclination of a specimen container for the specimen container loaded on a specimen rack including a plurality of container insertion ports which detachably hold the specimen container, a specimen transfer mechanism that has a plurality of arms which grip each side surface of the specimen containers, and a motor which drives the arms in an upward/downward direction, that transfers the specimen container to an empty container insertion port on the specimen rack, or that extracts the specimen container loaded on the specimen rack from a corresponding specimen container tray, and a control mechanism that controls each operation of the correction mechanism and the specimen transfer mechanism. The correction mechanism includes a first inclination correction holder that corrects the inclination of the specimen container of a first container insertion port accessed by the specimen transfer mechanism, a second inclination correction holder that corrects the inclination of the specimen container of a second container insertion port located at a position adjacent to the container insertion port, and a drive source that individually opens/closes the first inclination correction holder and the second inclination correction holder.

Advantageous Effects of Invention

The invention includes the above-described characteristics. Accordingly, when the specimen container is transferred to the transfer position, or when the transferred specimen container is removed, the specimen container located at the transfer position and the specimen container adjacent to the transfer position can be corrected to have a vertical posture without being inclined. Therefore, a transfer operation can be stably performed without the specimen container transfer mechanism and the specimen container coming into contact with each other.

DESCRIPTION OF EMBODIMENTS

Embodiments according to the invention will be described in detail with reference to the drawings.

Embodiment 1

Figure 1:
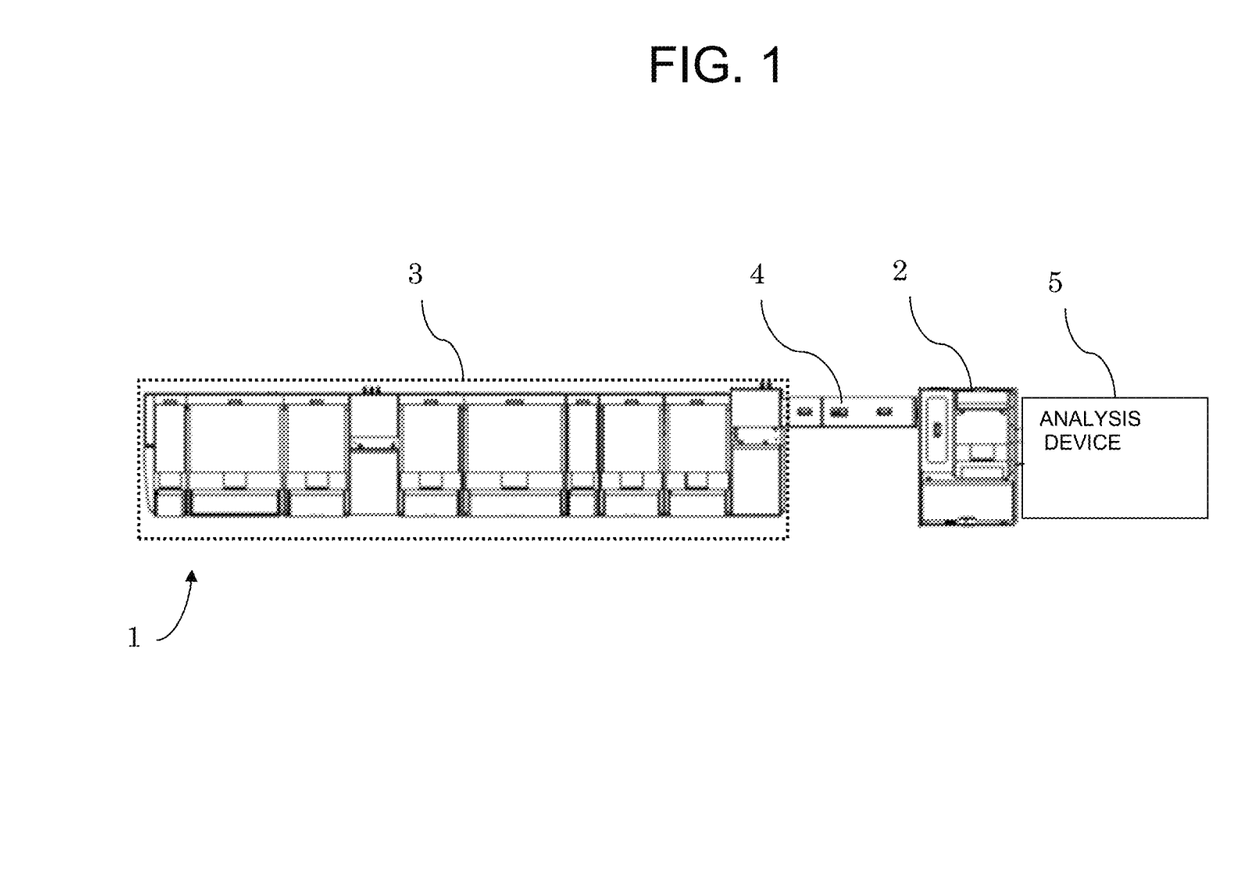
FIG. 1 is a schematic view illustrating a configuration example of a specimen transport system.

FIG. 1 is a schematic view illustrating a configuration example of a specimen transport system 1 whose partial configuration is a specimen container transfer device 2 having a specimen container inclination correction mechanism 22 loaded thereon according to an embodiment of the invention.

A specimen allocated from a pretreatment system 3 by an operator is loaded on a transport holder (not illustrated) held inside the specimen transport system 1, and is transported to a proper pretreatment unit by a transport device such as a belt conveyor. Depending on requested items, the specimen is subjected to processes such as centrifugation, cap opening, and dispensing inside the pretreatment system 3. The specimen is transported to the specimen transfer device 2 by way of a holder transport system 4. According to the present embodiment, a specimen holder holds a specimen container one by one.

In the invention, an analysis device 5 connected to the pretreatment system 3 via the specimen transfer device 2 performs an analysis process by loading the specimen container on a transport body having a type different from that of the transport holder. Therefore, the specimen transfer device 2 has the function to take the specimen container out of the transport holder so as to transfer the specimen container to a specimen rack (not illustrated) used in the analysis device 5. The specimen container transferred to the specimen rack is transported to the analysis device 5 so as to perform the analysis process. Furthermore, the specimen transfer device 2 may have a function to transfer the specimen container which is loaded on the specimen rack and whose analysis process is completed by the analysis device 5, to the transport holder.

Figure 2:
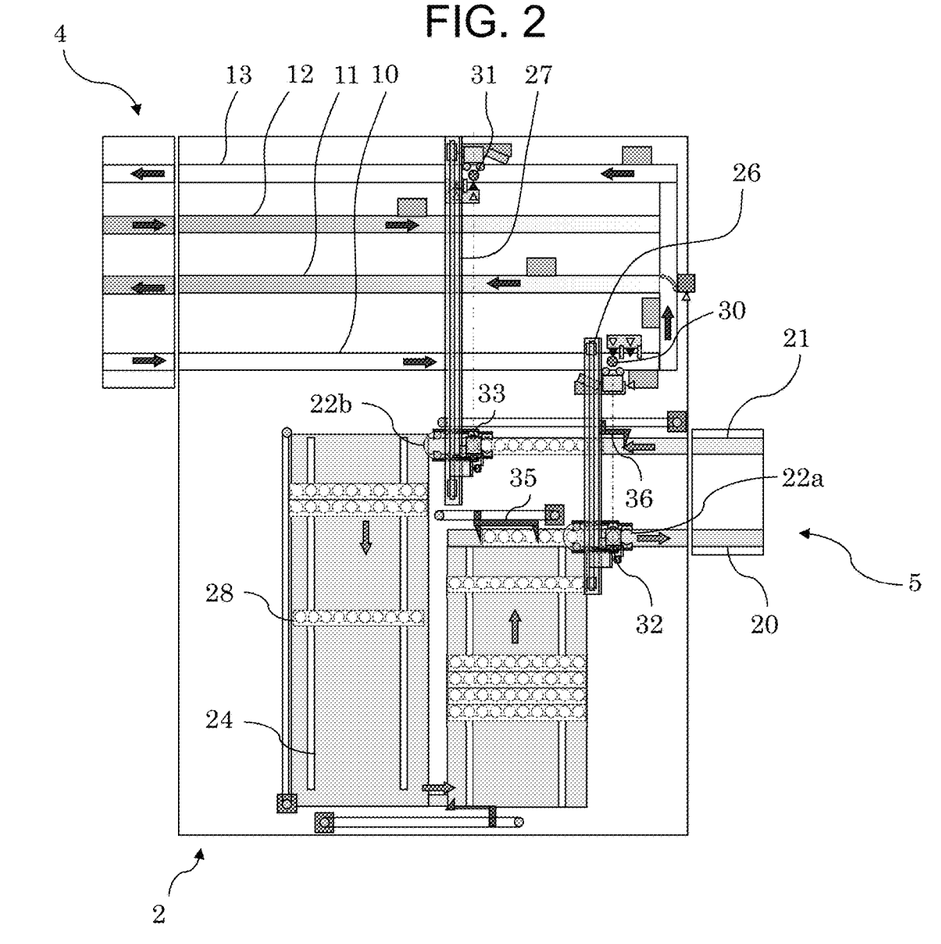
FIG. 2 is a block diagram illustrating a configuration example of a specimen container transfer mechanism.
Figure 3:
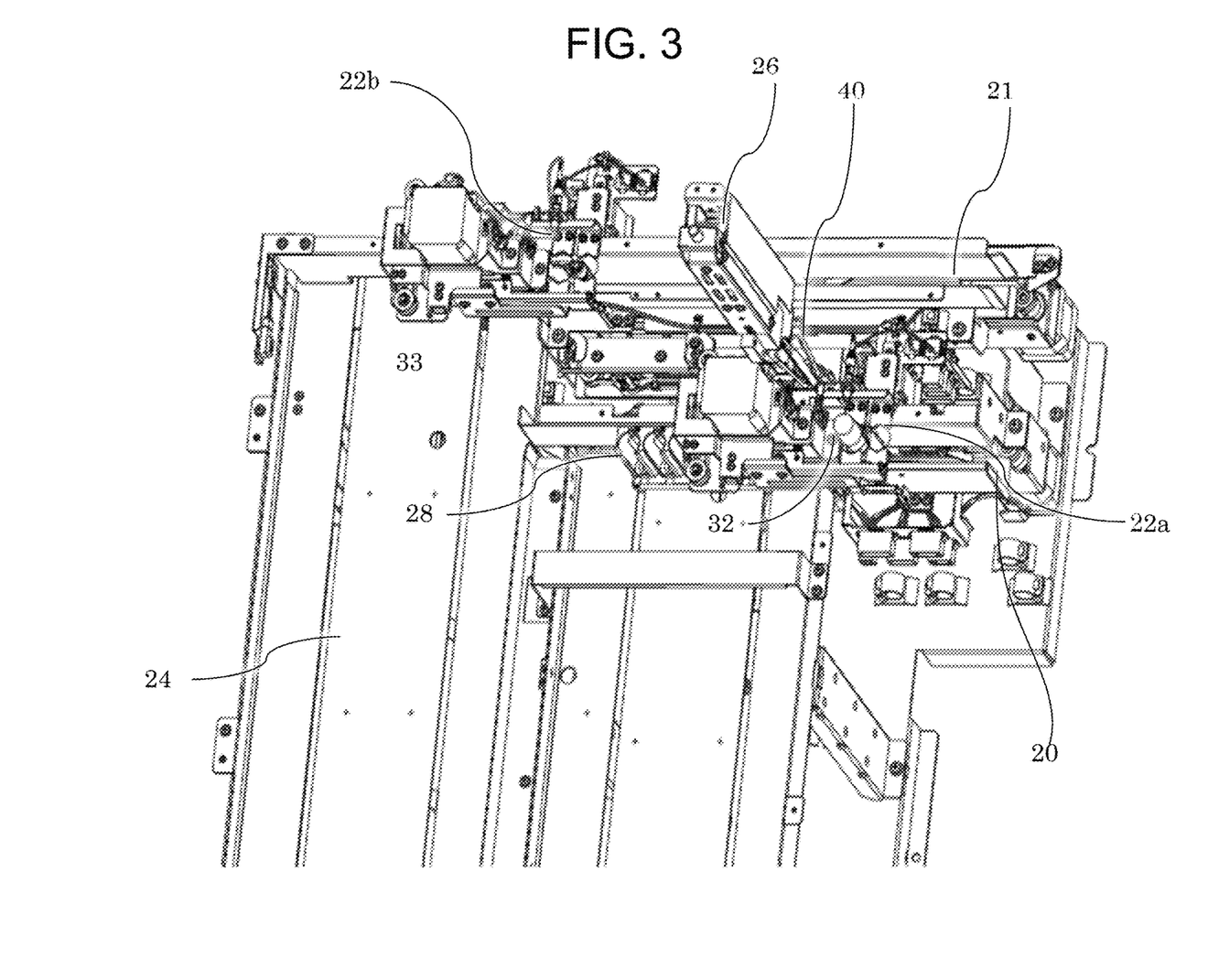
FIG. 3 illustrates a structure around a rack transport line of the specimen container transfer mechanism.

FIG. 2 is a schematic view illustrating a configuration example of the specimen container transfer device 2 according to an embodiment of the invention.

The specimen container transfer device 2 has a specimen holder supply line 10 that transports the specimen container installed in a holder for transporting the specimen transported from the holder transport system 4 to a supply holder-side specimen container transfer position 30, an empty holder collection line 11 that collects an empty holder after the specimen container is transferred to the specimen rack, a specimen holder return line 13 that receives the specimen container whose analysis is completed, at a return holder-side specimen container transfer position 31, and that transports the specimen container to the holder transport system 4, and an empty holder supply line 12 that supplies an empty holder to the specimen holder return line 13.

Furthermore, the specimen transfer device 2 has a rack buffer 24 that buffers a specimen rack 28 used for transporting the specimen inside the analysis device 5, a specimen rack supply line 20 that transports the specimen rack 28 from the rack buffer 24 to a supply rack-side specimen container transfer position 32, and that transports the specimen container to the analysis device 5 after the specimen container is transferred, and a specimen rack return line 21 that transports the specimen rack 28 from the analysis device 5 to a return rack-side specimen container transfer position 33, and that transports the specimen container to the rack buffer 24 after the specimen container is transferred. A plurality of the specimen racks 28 are loaded on the rack buffer 24. These specimen racks 28 are transported by two hooking units (not illustrated) which hook and push out the racks. Similarly, the specimen rack supply line 20 and the specimen rack return line 21 transport the specimen racks 28 by causing a hooking unit to hook an end surface of the specimen racks 28.

Furthermore, the specimen transfer device 2 has a supply-side specimen container transfer mechanism 26 that grips the specimen container loaded on the holder located on the specimen holder supply line 10, and that transfers the specimen container to the specimen rack located on the specimen rack supply line 20, and a return-side specimen container transfer mechanism 27 that grips the specimen container loaded on the specimen rack located on the specimen rack return line 21, and that transfers the specimen container to the holder located on the specimen holder return line 13.

Furthermore, the specimen transfer device 2 has a specimen container inclination correction mechanism 22a for the supply rack which corrects inclination of the specimen container at timing that the specimen container is transferred at the supply rack-side specimen transfer position 32 located on the specimen rack supply line 20, and a specimen container inclination correction mechanism 22b for the return rack which has a structure the same as that of the specimen container inclination correction mechanism 22a for the supply rack, and which is located at a return rack-side specimen transfer position 33 located on the specimen rack return line 21.

In the invention, the terms of "correction" of the specimen container includes not only holding the specimen container and maintaining the specimen container in an upright posture, but also surrounding the periphery and keeping an inclination angle of the specimen container within a predetermined range. For example, the following case may be employed. Not using a gripping force that is enough only to hold the specimen container, the specimen container is held using the gripping force which can extract the specimen container if the specimen container is pulled out by the specimen container transfer mechanism.

Figure 4:
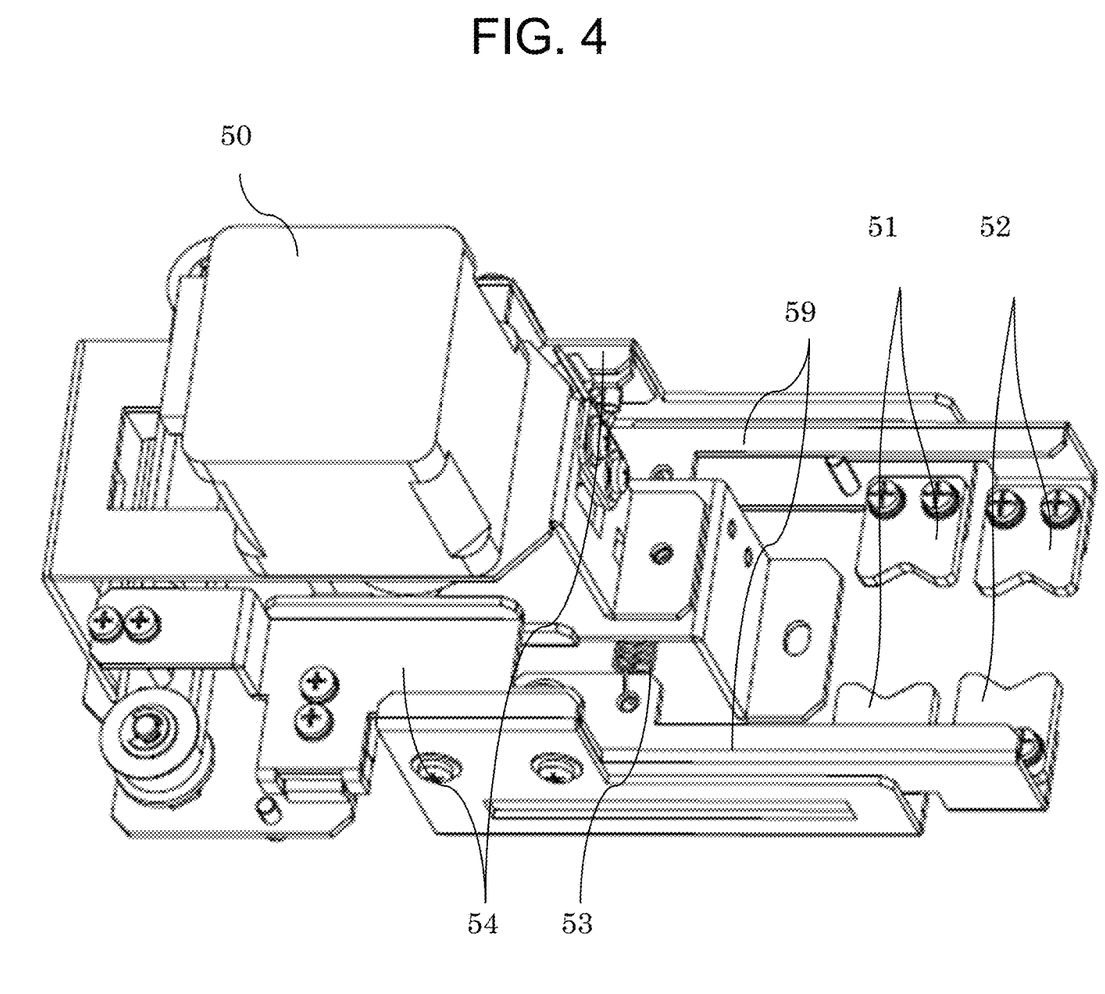
FIG. 4 illustrates a structure of a specimen container inclination correction mechanism.
Figure 5:
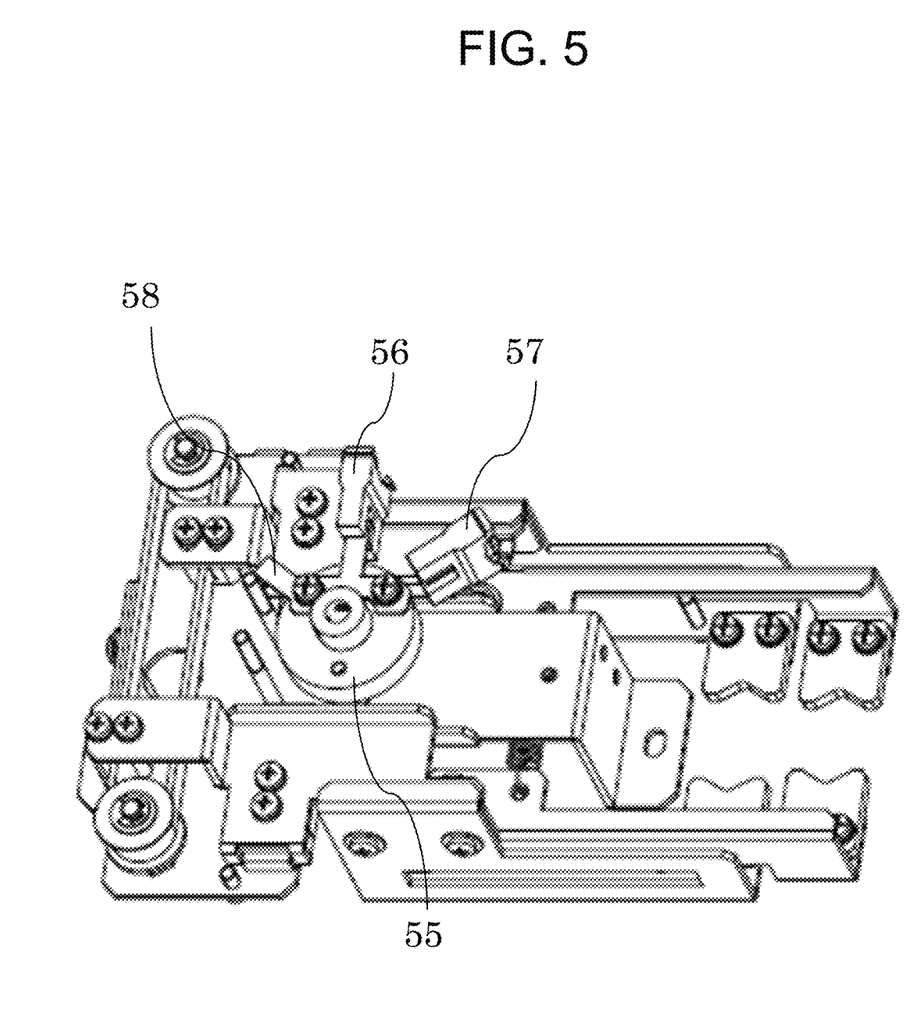
FIG. 5 illustrates a structure of a specimen container inclination correction mechanism (view in which a motor is not illustrated).

The specimen container inclination correction mechanism illustrated in FIGS. 4 and 5 has a pair of first inclination correction holders 51 which corrects the inclination angle for the specimen container located at the specimen container transfer position, a pair of second inclination correction holders 52 which corrects the inclination angle for the specimen container at a position adjacent to the first inclination correction holder 51, a motor 50 for driving the specimen container inclination correction mechanism which performs an operation for opening/closing the first inclination correction holder 51 and the second inclination correction holder 52, an elastic member 53, a pair of cams 55 fixed to a shaft of the motor 50, two detectors 56 and 57 for detecting an opened state and closed state of the first inclination correction holder 51 and the second inclination correction holder 52, and a detection member 58 fixed to the cam 55.

The pair of first inclination correction holders 51 includes a pair of first fixing members 54 (arms) disposed on both sides of the cam 55, and a correction member having a V-shaped recess which is disposed in the distal end of the arm and which comes into contact with an outer wall of the specimen container. Since such a correction member is provided, the inclination angle of the specimen container is suppressed. Accordingly, the specimen container can have an angle close to an upright angle.

Each of the second fixing members 59 (arms) is fixed to the first fixing member 54 so as to be rotatable around a shaft 60. The second inclination correction holder 52 is fixed to the distal end of the pair of second fixing members 59. In addition, an elastic member 53 is fixed to the pair of second fixing members 59, and a pulling force is applied in a direction in which the second inclination correction holders 52 move close to each other. A correction member having a shape the same as that of the first inclination correction holder 51 is disposed in the second inclination correction holder 51.

The cam 55 fixed to the shaft of the motor 50 is located inside the first fixing member 54, and the first fixing member 54 and the cam 55 are in contact with each other. If the motor 50 is rotated, the cam 55 is rotated together. The first fixing member 54 in contact with the cam 55 is operated in an opening/closing direction. In this manner, a mechanism is configured so that the first inclination correction holder 51 and the second inclination correction holder 52 are opened and closed.

Figure 7:
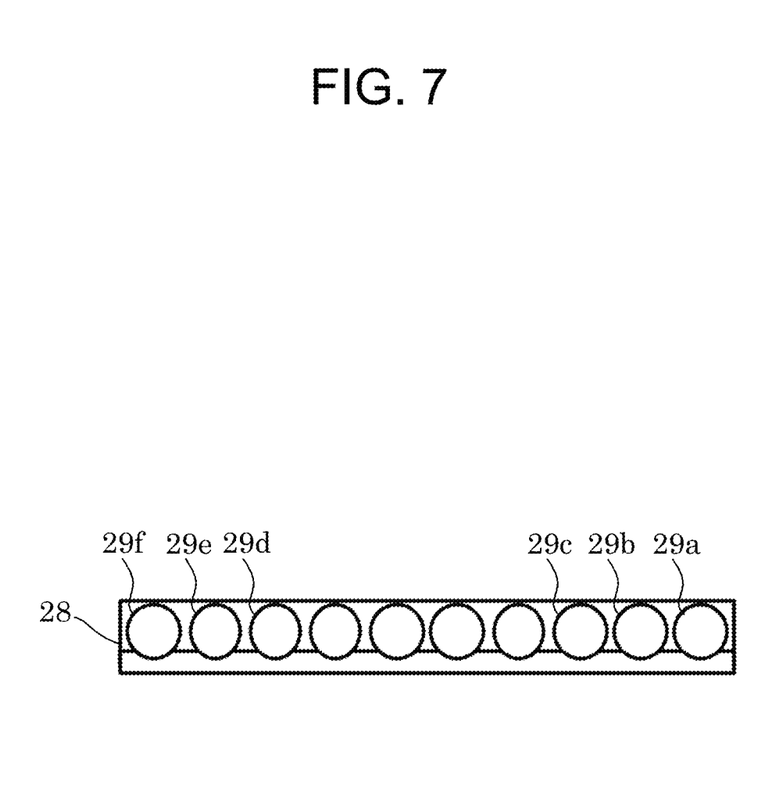
FIG. 7 is an outline view of a specimen rack.

A position relationship between the first inclination correction holder 51 and the second inclination correction holder 52 is the same as an interval of the positions 29 holding the specimen container on the specimen rack 28. The position relationship is as follows. The inclination of the specimen container transferred on the specimen rack 28 is corrected by the first inclination correction holder 51, and the inclination of the specimen container adjacent thereto is corrected by the second inclination correction holder 52.

In addition, the maximum opening amount of the first inclination correction holder 51 is larger than the maximum opening amount of the second inclination correction holder 52. The present embodiment is configured so that the first inclination correction holder 51 is more widely opened as large as 4 mm. In this manner, it is possible to close the second inclination correction holder 52 while the first inclination correction holder 51 remains in an opened state.

Figure 6:
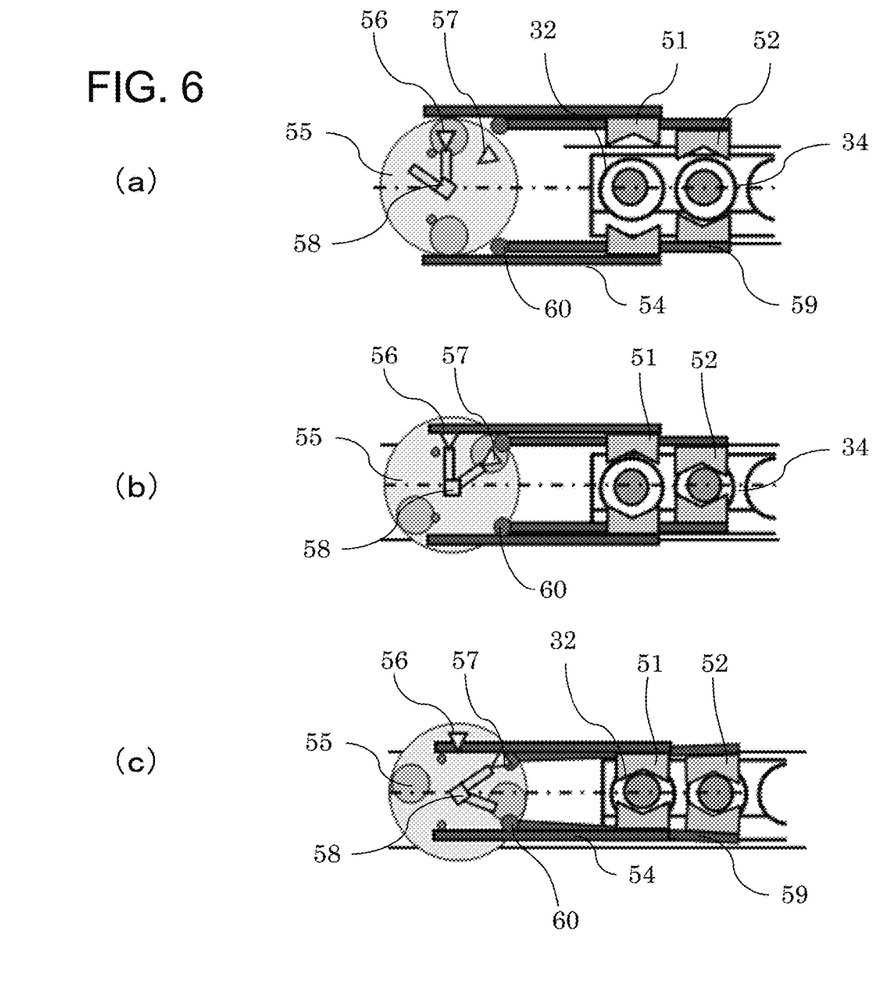
FIG. 6 is a block diagram illustrating an operation of the specimen container inclination correction mechanism.

If the motor 50 of the specimen container inclination correction mechanism 22 is rotated, the cam 55 and the detection member 58 which are fixed to the shaft of the motor 50 are rotated together. In the present embodiment, the detection member has a V-shape in which two detection rods are arranged to form a predetermined angle. In a state where the detection member 58 is inserted into only the first detector 56 (FIG. 6(a)), the cam 55 spreads the first fixing member 54, and the second fixing member 59 connected to the first fixing member via the shaft 60 is also brought into the opened state. Therefore, both the first inclination correction holder 51 and the second inclination correction holder 52 are in the opened state. In this state, even if the specimen container loaded on the specimen rack passes under the specimen container inclination correction mechanism 22, the inclination correction unit does not come into contact with the specimen container.

In a state where the detection member 58 is inserted into both the detector 56 and the detector 57 (FIG. 6(b)), a contact state between the cam 55 and the first fixing member 54 is changed. In this manner, the first fixing member 54 and the second fixing member 59 are brought into a slightly closed state compared to the state illustrated in FIG. 6(a). The contact state between the cam 55 and the first fixing member 54 is not completely released. Accordingly, the first inclination correction holder 51 is in the opened state. However, the second inclination correction holder 52 is fixed with a flat width narrower than that of the first inclination correction holder 51. Accordingly, the second inclination correction holder 52 is brought into a closed state. Therefore, the inclination of the specimen container loaded at the adjacent position 34 of the specimen container which is a target transferred by the specimen transfer mechanism is corrected on the specimen rack.

The terms of "the closed state" described herein means a state where a function to correct the inclination of the specimen container is fulfilled by the inclination correction unit coming into contact with at least one point of a wall surface of the specimen container. The closed state does not necessarily indicate only a state where the outer wall of the specimen container is fixedly held. In addition, "the opened state" means that the outer wall is not in the closed state.

In a state where the detection member 58 is inserted into only the detector 57 (FIG. 6(c)), the cam 55 and the first fixing portion 54 are not in a complete contact state. In this case, both the first fixing portion 54 and the second fixing portion 59 are pulled in a closing direction by the tension of the elastic member 53, and both the first inclination correction holder 51 and the second inclination correction holder 52 are in the closed state. Therefore, the inclination of both the specimen container of the transfer target and the specimen container located at the adjacent position 34 of the specimen container is corrected by the specimen container transfer mechanism.

As described above, the motor 50 including the cam is rotated, and the contact state between the cam and the first fixing member 54 is adjusted. In this manner, an opening/closing state of the first inclination correction holder 51 and the second inclination correction holder 52 can be individually controlled. According to this mechanism, when the transfer mechanism transfers the specimen container to the empty position on the rack or extracts the specimen container held on the rack in order to transfer the specimen container to another place, the transfer mechanism corrects the inclination of the specimen container located at the position accessed by the transfer mechanism and the specimen container located at the adjacent position 34. Therefore, it is possible to eliminate the contact risk between the specimen container and the transfer mechanism.

A shape of the correction member illustrated in FIGS. 4 and 5 is merely an example, and the correction member is not limited to this shape. For example, the correction member may have a type provided with a position relationship where a plurality of rollers can pinch the specimen container. In addition, the correction member may have a surrounding shape which simply surrounds the specimen container. In short, any configuration may be adopted as long as it is possible to suppress the contact between the specimen container and specimen container adjacent thereto or the specimen container transfer mechanism by inclining the specimen container.

In addition, the detection member 58 is not limited to the V-shape. In the invention, the inclination correction mechanism employs a three-stage state, and thus, the inclination is identified by turning on/off two detectors. However, in a case where the employed state has three or more stages, the inclination correction mechanism may include the more detectors and detection members.

In addition, the transfer of the specimen container in the invention is not necessarily limited to the transfer between the holder and the specimen rack. For example, the inclination correction mechanism may be disposed between the specimen tray having the specimen containers arrayed thereon and the rack holder when the specimen container is transferred. In this case, for example, the specimen container inclination correction mechanism 22 is also disposed above the tray side so as to correct the inclination of the specimen container located at the specimen transfer position on the tray and the specimen container adjacent thereto.

Embodiment 2

First, control in a case where the specimen container loaded on the holder is transferred to the specimen rack capable of loading ten specimen containers will be described.

In a state where the specimen container allocated to the pretreatment system 3 is loaded on the holder, the specimen container is transported and is subjected to processes such as centrifugation, cap opening, and dispensing. Thereafter, the specimen container passes through the holder transport system 4, and is transported to the specimen container transfer device 2. The specimen container transported to the specimen container transfer device 2 is transported to the supply holder-side specimen container transfer position 30 located on the specimen holder supply line 10, and waits for the subsequent process.

On the other hand, on the rack transport side, the specimen rack 28 waiting for the subsequent process in the rack buffer 24 is transported to the specimen rack supply line 20. Thereafter, the end surface of the rack is pushed by the supply rack transport mechanism 35 which operates the specimen rack 28 on the specimen rack supply line 20, thereby moving the specimen rack 28 until the position 29a of the specimen rack 28 reaches the supply rack-side specimen container transfer position 32 of the specimen rack supply line 20.

The supply-side specimen container transfer mechanism includes a movement mechanism having a plurality of openable/closable arms (specimen container chuck 40), a drive source such as a motor and a solenoid for opening/closing the arms, and a rail mechanism for moving the arms in an upward/downward direction. The supply-side specimen container transfer mechanism 26 moves to above the specimen container transported to the supply holder-side specimen container transfer position 30 on the specimen holder supply line 10, and is lowered after opening the specimen container chuck 40. After being lowered, the specimen container chuck 40 is closed, and the specimen container is gripped. The specimen container is raised, and is extracted from the holder.

Next, the supply-side specimen container transfer mechanism 26 moves to above the position 29a of the specimen rack 28 located at the supply rack-side transfer position 32 in a state where the specimen container chuck 40 grips the specimen container. At this time, as illustrated in FIG. 6(b), the supply rack specimen container inclination correction mechanism 22a rotates the motor 50, and is stopped after inserting the detection member 58 into both the detector 56 and the detector 57. In this manner, the first inclination correction holder 51 is brought into an opened state, and the second inclination correction holder 52 is brought into a closed state. However, in this case, the position 29a has the specimen container transferred first. Accordingly, the specimen container is not installed at the adjacent position, and the second inclination correction holder 52 does not come into contact with the outer wall of the specimen container. In this way, when the first specimen container is transferred, it is unlikely to happen that the specimen container adjacent thereto is inclined to inhibit the transfer process of the specimen container. Therefore, the process for switching to a state in FIG. 6(b) may be omitted.

The supply-side specimen container transfer mechanism 26 is lowered, and is inserted into the position 29a of the specimen rack 28. If the specimen container chuck 40 is opened, and it is detected that the specimen container is completely transferred, as illustrated in FIG. 6(c), the supply rack specimen container inclination correction mechanism 22a rotates the motor 50, and is stopped after the mode is switched to a state where the detection member 58 is detected by only the detector 57. In this manner, both the first inclination correction holder 51 and the second inclination correction holder 52 are brought into a closed state. Thus, the inclination of the transferred specimen container to the position 29a can be corrected. Then, the supply-side specimen container transfer mechanism 26 opens the specimen container chuck 40, and releases the specimen container. The supply-side specimen container transfer mechanism 26 is raised, and the specimen container is completely transferred to the position 29a.

The specimen container inclination correction mechanism 22 corrects the inclination of the specimen container loaded at the position 29a. Accordingly, when the supply-side specimen container transfer mechanism 26 is raised, it is possible to suppress the risk that the specimen container chuck 40 and the specimen container loaded at the position 29a may come into contact with each other.

After the supply-side specimen container transfer mechanism 26 is raised, the supply rack specimen container inclination correction mechanism 22a rotates the motor 50 as illustrated in FIG. 6(a), and is stopped after inserting the detection member 58 into only the detector 56. In this manner, both the first inclination correction holder 51 and the second inclination correction holder 52 are brought into an opened state, thereby stopping an operation for suppressing the inclination of the specimen container. Thereafter, the supply rack transport mechanism 35 pushes the specimen rack 28, transports the specimen rack 28 until the position 29b reaches the supply rack-side specimen container transfer position 32, and waits for the subsequent process.

Subsequently, if the second specimen container is transported to the transfer position on the specimen holder supply line 10, similarly to the first specimen container, the supply-side specimen container transfer mechanism 26 moves to the supply holder-side specimen container transfer position 30, opens the specimen container chuck 40, and is lowered. If the second specimen container is gripped, the supply-side specimen container transfer mechanism 26 is raised, and moves again to the supply rack specimen container transfer position 32.

Here, similarly to when the first specimen container is transferred as described above, the supply rack specimen container inclination correction mechanism 22a rotates the motor 50 as illustrated in FIG. 6(b), and is stopped after inserting the detection member 58 into both the detector 56 and the detector 57. Thus, the first inclination correction holder 51 is brought into an opened state, and the second inclination correction holder 52 is brought into a closed state. In this manner, the inclination of the first specimen container loaded at the adjacent position 34 of the supply rack specimen container transfer position, that is, at the position 29a, is corrected by the second inclination correction holder 52 so as to have an upright posture. Even if the specimen container is loaded at the position 29a, this configuration suppresses the risk that the specimen container may be greatly inclined and may come into contact with the supply-side specimen container transfer mechanism 26 or the specimen container transported by the supply-side specimen container transfer mechanism 26.

While maintaining this state, the supply-side specimen container transfer mechanism 26 is lowered, and the specimen container is inserted into the position 29b of the rack. After the lowering operation, similarly to when the first specimen container is transferred, the supply rack specimen container inclination correction mechanism 22a rotates the motor 50 as illustrated in FIG. 6(c), and is stopped after inserting detection member 58 into only the detector 57. Thus, both the first inclination correction holder 51 and the second inclination correction holder 52 are brought into a closed state. In this manner, it is possible to suppress not only the inclination of the specimen container inserted into the position 29a, but also the inclination of the specimen container inserted into the position 29b.

The specimen container transfer mechanism 26 opens the specimen container chuck 40, and releases the specimen container transferred to the position 29b. Thereafter, the supply-side specimen container transfer mechanism 26 is raised, and the specimen rack 28 is completely transferred to the position 29b. In this case, the specimen container inclination correction mechanism 22 also causes both the first inclination correction holder 51 and the second inclination correction holder 52 to suppress the inclination of the specimen containers located at the position 29a and the position 29b. Accordingly, the specimen container transfer mechanism 22 can be raised without coming into contact with the specimen container.

After the specimen rack 28 is completely transferred to the position 29b, the supply rack specimen container inclination correction mechanism 22a rotates the motor 50 as illustrated in FIG. 6(a), and is stopped after inserting the detection member 58 into only the detector 56. Both the first inclination correction holder 51 and the second inclination correction holder 52 are opened so as to stop correcting the inclination of the specimen container.

Subsequently, the specimen rack supply line 20 moves the specimen rack 28 so that the position 29c of the specimen rack 28 reaches the transfer position, and prepares for the transfer of the next specimen container. If the specimen container is completely transferred to the position 29f of the specimen rack 28 by using the above-described transfer method, the specimen rack 28 is transported from the specimen rack supply line 20, and is transported to the analysis device 5.

Embodiment 3

Next, control in a case where the specimen containers loaded on the specimen rack having the plurality of specimen containers loaded thereon are transferred to the holder one by one will be described.

The specimen container whose analysis process is completed in the analysis device 5 is transported from the analysis device 5 in a state where the specimen container is loaded on the specimen rack 28, and is transported to the specimen container transfer device 2. In the specimen rack 28, the specimen containers are inserted into all of the positions 29. After the specimen rack 28 is transported to the specimen rack return line 21 of the specimen container transfer device 2, the specimen rack 28 is transported until the position 29f of the specimen rack 28 directly reaches the return rack-side specimen container transfer position 33 on the specimen rack return line 21. At this time, similarly to the specimen rack supply line 20 according to Embodiment 1, the transporting method of the specimen rack 28 is configured so that the specimen rack 28 is transported by pushing the end surface of the specimen rack 28 by the return rack transport mechanism 36.

At this time, the return-side specimen container transfer device 27 rotates the motor 50 as illustrated in FIG. 6(a) so that the specimen container inserted into the specimen rack 28 does not collide with the first inclination correction holder 51 and the second inclination correction holder 52 of the return-side specimen container transfer device 27, and is stopped after inserting the detection member 58 into only the detector 56. Both the first inclination correction holder 51 and the second inclination correction holder 52 are brought into an opened state.

Thereafter, the specimen rack 28 is transported until the position 29f reaches the return rack-side specimen container transfer position 33, and the return-side specimen container transfer device 27 moves to above the position 29f of the specimen rack 28.

Here, the return rack specimen container inclination correction mechanism 22b rotates the motor 50 as illustrated in FIG. 6(c), and is stopped after inserting the detection member 58 into only the detector 57. Both the first inclination correction holder 51 and the second inclination correction holder 52 are brought into a closed state. This configuration suppresses the inclination of the specimen container located at the position 29f of the specimen rack 28 and the specimen container located at the position 29e adjacent thereto.

If the return rack specimen container inclination correction mechanism 22b suppresses the inclination of the specimen container, the return-side specimen container transfer mechanism 27 opens the specimen container chuck 40, and is lowered to the position 29f. At this time, the inclination of the specimen containers loaded at the positions 29f and 29e is suppressed by the return rack specimen container inclination correction mechanism 22b. Accordingly, the return-side specimen container transfer mechanism 27 can be smoothly lowered without the specimen container chuck 40 and the specimen container coming into contact with each other.

After being lowered, the specimen container chuck 40 is closed so as to grip the specimen container. If it is detected that the specimen container chuck 40 is closed, the return rack specimen container inclination correction mechanism 22b rotates the motor 50 as illustrated in FIG. 6(b), and is stopped after inserting the detection member 58 into both the detector 56 and the detector 57. In this manner, the first inclination correction holder 51 is brought into an opened state, and the second inclination correction holder 52 is brought into a closed state. Therefore, the inclination correction of the specimen container located at the position 29f is released, and the specimen container chuck 40 is closed and raised in the return-side specimen container transfer mechanism 27. The return-side specimen container transfer mechanism 27 extracts the specimen container loaded at the position 29f from the specimen rack. At this time, the specimen container located at the position 29e is still brought into a state where the inclination is suppressed by the second inclination correction holder 52. Accordingly, when the specimen container located at the position 29f is pulled out, the specimen container chuck 40 or the specimen container does not come into contact with and does not collide with the specimen container located at the position 29e.

After being raised, the return-side specimen container transfer mechanism 27 moves to the return holder-side specimen container transfer position 31 on the specimen holder return line 13, is lowered again, and inserts the specimen container into the holder. Thereafter, the return-side specimen container transfer mechanism 27 opens the specimen container chuck 40, is raised again, and the specimen container is completely transferred to the position 29f of the specimen rack 28.

After the return-side specimen container transfer mechanism 27 is raised, the return-side specimen container transfer device 27 rotates the motor 50 as illustrated in FIG. 6(a), and is stopped after inserting the detection member 58 into only the detector 56. Both the first inclination correction holder 51 and the second inclination correction holder 52 are brought into an opened state. The specimen rack return line 21 operates the return rack transport mechanism 36 so as to move the position 29e of the specimen rack 28 to the return rack-side specimen container transfer position 33.

Subsequently, the specimen container located at the position 29e of the specimen rack 28 starts to be transferred. The operation is similar to the transfer operation performed at the position 29f. The specimen container transferred to the holder passes through the holder transport system 4 after the specimen container transfer device 2 is transported, and is transported to the pretreatment system 3 so as to be stored. After all of the specimen containers up to the position 29a are completely transferred, the specimen rack 28 is transported from the specimen rack return line 21, and is transported to the rack buffer 24. The specimen rack 28 is reused by transferring the arrived specimen container to the subsequent specimen holder supply line 10.

Herein, an embodiment has been described as follows. When the specimen container located at the return rack-side specimen container transfer position 33 is pulled out, only the first inclination correction holder 51 of the specimen container inclination correction mechanism 22 is opened, and the specimen container is pulled out by the specimen container transfer mechanism 27. However, without performing the operation for opening the first inclination correction holder 51, the first inclination correction holder 51 can also be pulled out using a member having a small frictional force such as the first inclination correction holder 51 whose shape is a roller. In this case, the first inclination correction mechanism. 22 is brought into a state illustrated in FIG. 6(c). While the inclination of the specimen container is corrected, the specimen chuck mechanism unit 40 is raised so as to extract the specimen container.

In the above-described embodiments, an example has been described in which the specimen container is transferred to/from the specimen rack for transporting the specimen container. However, instead of the transporting rack, the rack may be used for storing and holding the specimen container. In addition, not only the rack may have the plurality of insertion ports juxtaposed with each other, but the rack (tray) may have two-dimensional insertion ports juxtaposed with each other in both rows and lines.

Furthermore, the first inclination correction holder 51 and the second inclination correction holder 52 are opened and closed by the same motor 50. However, the invention is not limited thereto. An individual drive source may be provided for each inclination correction unit.

REFERENCE SIGNS LIST

1 SPECIMEN TRANSPORT SYSTEM
2 SPECIMEN CONTAINER TRANSFER DEVICE
3 PRETREATMENT SYSTEM
4 HOLDER TRANSPORT SYSTEM
5 ANALYSIS DEVICE
10 SPECIMEN HOLDER SUPPLY LINE
11 EMPTY HOLDER COLLECTION LINE
12 EMPTY HOLDER SUPPLY LINE
13 SPECIMEN HOLDER RETURN LINE
20 SPECIMEN RACK SUPPLY LINE
21 SPECIMEN RACK RETURN LINE
22a SUPPLY RACK SPECIMEN CONTAINER INCLINATION CORRECTION MECHANISM
22b RETURN RACK SPECIMEN CONTAINER INCLINATION CORRECTION MECHANISM
24 RACK BUFFER
26 SUPPLY-SIDE SPECIMEN CONTAINER TRANSFER MECHANISM
27 RETURN-SIDE SPECIMEN CONTAINER TRANSFER MECHANISM
28 SPECIMEN RACK
29a TO f POSITION
30 SUPPLY HOLDER-SIDE SPECIMEN CONTAINER TRANSFER POSITION
31 RETURN HOLDER-SIDE SPECIMEN CONTAINER TRANSFER POSITION
32 SUPPLY RACK-SIDE SPECIMEN CONTAINER TRANSFER POSITION
33 RETURN RACK-SIDE SPECIMEN CONTAINER TRANSFER POSITION
34 ADJACENT POSITION
35 SUPPLY RACK TRANSPORT MECHANISM
36 RETURN RACK TRANSPORT MECHANISM
40 SPECIMEN CONTAINER CHUCK
50 MOTOR
51 FIRST INCLINATION CORRECTION HOLDER
52 SECOND INCLINATION CORRECTION HOLDER
53 ELASTIC MEMBER
54 FIRST FIXING MEMBER
55 CAM
56, 57 DETECTOR
58 DETECTION MEMBER
59 SECOND FIXING MEMBER
60 SHAFT

The invention claimed is:

1. A specimen transport system comprising:
a first system that treats a specimen container loaded on a first specimen rack;
a second system that treats a plurality of specimen containers loaded on a second specimen rack; and
a specimen transfer device that is disposed between the first system and the second system,
wherein the specimen transfer device includes
a correction mechanism that corrects inclination of the specimen containers for the specimen containers loaded on a plurality of container insertion ports which detachably hold the specimen containers on the second specimen rack, and
a specimen transfer mechanism that has a plurality of arms which grip each side surface of the specimen containers, and a motor which drives the arms in an upward/downward direction, that transfers the specimen container to an empty container insertion port on the second specimen rack, or that extracts the specimen container loaded on the second specimen rack from the second specimen rack,
wherein the correction mechanism includes a first inclination correction holder that corrects the inclination of the specimen container of a first container insertion port accessed by the specimen transfer mechanism,
a second inclination correction holder that corrects the inclination of the specimen container of a second container insertion port located at a position adjacent to the first container insertion port, a drive source that individually opens/closes the first inclination correction holder and the second inclination correction holder, a first arm that opens/closes the first inclination correction holder, a second arm that is fixed to the first arm so as to be relatively movable, and that opens/closes the second inclination correction holder, and a cam that comes into contact with the first arm so that the first arm and the second arm are brought into an opened state or a closed state by using a rotation angle, wherein the drive source is a motor connected to the cam, and wherein the rotation angle of the cam is controlled by the motor so as to control the opened state or the closed state of the first arm and the second arm.

2. The specimen transport system according to claim 1, wherein if the specimen transfer mechanism transfers the specimen container to the first container insertion port, the first inclination correction holder and the second inclination correction holder correct each inclination of the specimen containers of the first container insertion port and the second container insertion port, and then, the specimen transfer mechanism raises the arms in an opened state.

3. The specimen transport system according to claim 1, wherein if the specimen container is transferred to the first container insertion port, the first inclination correction holder and the second inclination correction holder correct each inclination of the specimen containers of the first container insertion port and the second container insertion port, and then, the specimen transfer mechanism raises the arms in an opened state.

4. The specimen transport system according to claim 1, wherein the first system is a specimen pretreatment system, and wherein the second system is a specimen analysis system.

5. A specimen transfer device comprising:

a correction mechanism that corrects inclination of a specimen container for the specimen container loaded on a specimen rack including a plurality of container insertion ports which detachably hold the specimen container;

a specimen transfer mechanism that has a plurality of arms which grip each side surface of the specimen containers, and a motor which drives the arms in an upward/downward direction, and that transfers the specimen container to an empty container insertion port on the specimen rack, or that extracts the specimen container loaded on the specimen rack from the specimen rack; and wherein the correction mechanism includes a first inclination correction holder that corrects the inclination of the specimen container of a first container insertion port accessed by the specimen transfer mechanism, a second inclination correction holder that corrects the inclination of the specimen container of a second container insertion port located at a position adjacent to the first container insertion port, a drive source that individually opens/closes the first inclination correction holder and the second inclination correction holder, a first arm that opens/closes the first inclination correction holder, a second arm that is fixed to the first arm so as to be relatively movable, and that opens/closes the second inclination correction holder, and a cam that comes into contact with the first arm so that the first arm and the second arm are brought into an opened state or a closed state by using a rotation angle, wherein the drive source is a motor connected to the cam, and wherein the rotation angle of the cam is controlled by the motor so as to control the opened state or the closed state of the first arm and the second arm.

6. The specimen transfer device according to claim 5, wherein if the specimen transfer mechanism transfers the specimen container to the first container insertion port, the first inclination correction holder and the second inclination correction holder correct each inclination of the specimen containers of the first container insertion port and the second container insertion port, and then, the specimen transfer mechanism raises the arms in an opened state.

7. specimen transfer device according to claim 5, wherein if the specimen container is transferred to the first container insertion port, the first inclination correction holder and the second inclination correction holder correct each inclination of the specimen containers of the first container insertion port and the second container insertion port, and then, the specimen transfer mechanism raises the arm in an opened state.

* * * * *